(12) United States Patent
Dallafior

(10) Patent No.: US 9,125,727 B2
(45) Date of Patent: Sep. 8, 2015

(54) SMART BANDS ELASTIC BANDAGES

(71) Applicant: Dave Dallafior, Bedminster, NJ (US)

(72) Inventor: Dave Dallafior, Bedminster, NJ (US)

(73) Assignee: DVR PLUS LLC, Bernardsville, NJ (US)

( * ) Notice: Subject to any disclaimer, the term of this patent is extended or adjusted under 35 U.S.C. 154(b) by 247 days.

(21) Appl. No.: 13/681,465

(22) Filed: Nov. 20, 2012

(65) Prior Publication Data

US 2013/0131565 A1    May 23, 2013

Related U.S. Application Data

(60) Provisional application No. 61/563,101, filed on Nov. 23, 2011.

(51) Int. Cl.
```
A61F 5/01      (2006.01)
A61F 13/00     (2006.01)
A61F 13/84     (2006.01)
```

(52) U.S. Cl.
CPC ............. *A61F 5/01* (2013.01); *A61F 13/00038* (2013.01); *A61F 2013/00119* (2013.01); *A61F 2013/00153* (2013.01); *A61F 2013/8497* (2013.01)

(58) Field of Classification Search
USPC ................ 602/41–59, 75–79; 73/760, 862.39
See application file for complete search history.

(56) References Cited

U.S. PATENT DOCUMENTS

| | | | | |
|---|---|---|---|---|
| 1,104,575 A * | 7/1914 | Swope | ............................. | 602/78 |
| 3,529,601 A * | 9/1970 | Kirkland | ........................ | 604/312 |
| 3,613,679 A * | 10/1971 | Bijou | ............................... | 602/75 |
| 5,195,950 A * | 3/1993 | Delannoy | ........................ | 602/75 |
| 5,779,659 A | 7/1998 | Allen | | |
| 6,142,968 A * | 11/2000 | Pigg et al. | ........................ | 602/75 |
| 6,822,133 B2 * | 11/2004 | Lebner | ............................. | 602/54 |
| 8,372,024 B1 * | 2/2013 | Henderson | ........................ | 602/75 |
| 2002/0099318 A1 * | 7/2002 | Suehr et al. | ........................ | 602/76 |
| 2011/0071453 A1 | 3/2011 | Schuren et al. | | |

FOREIGN PATENT DOCUMENTS

| | | |
|---|---|---|
| GB | 2194932 A | 3/1988 |
| GB | 2355431 A | 4/2001 |
| JP | 5046093 B2 | 10/2012 |
| WO | 2006118840 A1 | 11/2006 |

\* cited by examiner

*Primary Examiner* — Kim M Lewis
(74) *Attorney, Agent, or Firm* — Cowan, Liebowitz & Latman P.C.; Mark Montague; Serge Krimnus

(57) ABSTRACT

An elastic bandage having an elongated length in which the bandage has a portion that extends along its length that is of a shade of a color that is a function of the amount the material is stretched, representing either a loose fit, a firm fit, or a tight fit. A novel color chart may be used with the elastic bandage that includes different shades printed thereon to assist the user during wrapping of the bandage around a part of a body. The elastic bandage may further include a second portion that extends along its length that is of a color different from the first portion and wherein, upon completion of a proper wrapping of the bandage, most of the first color of the first portion is visible and nearly none of the second color of the second portion is visible. The elastic bandage may further have a different color on its opposite side wherein the user places that opposite side down, toward the body part to be wrapped, and then upon completion of wrapping, an enclosure mechanism can properly be used to prevent the bandage from unraveling.

17 Claims, 4 Drawing Sheets

SMART BANDS ELASTIC BANDAGES

REFERENCE TO RELATED APPLICATION

This application claims priority to U.S. Provisional Patent Application No. 61/563,101, filed Nov. 23, 2011, the disclosure of which is incorporated herein by reference.

BACKGROUND OF THE INVENTION

1. Field of the Invention

The present invention is directed to novel elastic bandages, also referred to herein as Smart Bands™ elastic bandages, and particularly is directed to novel elastic bandages that provide beneficial features that are not provided by currently available elastic bandages.

2. Description of the Related Art

An elastic bandage, sometimes referred to as a compression bandage, is stretchable and when properly used provides localized pressure and support. Elastic bandages are most commonly used after a part of the body, such as a leg, ankle, arm or wrist, is injured. For example, elastic bandages are used to provide support to an area of the body to prevent further injury, reduce or prevent swelling, maintain injured bones or a device (e.g., a splint) in proper position and other reasons.

Currently existing elastic bandages are fairly basic. Existing elastic bandages are white or flesh-tone in color and are made of latex as well as non-latex woven or knitted materials. More recently manufactured elastic bandages are made of cotton, polyester and latex-free elastic yarns. Such bandages use metal clips or Velcro® (i.e., hook and loop fastener) as fasteners to keep the bandages from unraveling. In addition to being worn on the arms, wrists, legs, and ankles, elastic bandages also have been worn on other parts of the body, such as around the torso as a sort of body wrap for weight loss, back support and other reasons.

Ordinarily, a medical provider, such as a doctor, physician's assistant or nurse, wraps an elastic bandage around a part of an individual's body during a visit to a medical office, typically after incurring an injury, or after the individual undergoes a medical procedure. Usually, the medical provider wraps the elastic bandage quickly, professionally and properly. The medical provider typically has substantial experience in wrapping elastic bandages, is well aware of the amount of support and pressure the elastic bandage needs to provide to the injured and/or recovering body part, and accordingly wraps the elastic bandage around the body part in a manner to provide such necessary support and pressure. Typically, the medical provider does not provide the patient with any guidance as to how to re-wrap the elastic bandage after it is removed, such as to wash the body part. At most, the medical provider indicates that the elastic bandage should be re-applied in the same manner as carried out by the medical provider.

The above-summarized scenario unfortunately often results in an individual's inability to properly re-wrap the elastic bandage around the relevant body part. Many, if not most, people who are not trained medical providers are not able to remember exactly how to apply the elastic bandage. Individuals simply estimate or guess how the elastic bandage is to be re-applied. As a result, re-applied elastic bandages often do not provide the proper amount of support and pressure that are needed to maximize recovery, or to otherwise maximize the intended benefits of using elastic bandages.

Despite the foregoing, no elastic bandage products currently are offered for sale that enable non-trained individuals to properly apply or re-apply bandages.

OBJECTS AND SUMMARY OF THE INVENTION

It is an object of the present invention to provide a novel elastic bandage that includes one or more novel features so as to, in general, enable non-trained individuals to properly use the bandage.

It is a further object of the present invention to provide a novel elastic bandage that provides beneficial features that are not provided by currently available elastic bandages.

It is another object of the present invention to provide a novel elastic bandage that enables an individual to properly wrap the bandage around a body part so that the bandage applies the proper amount of pressure to the wrapped body part.

These and other objects are further discussed below. Having described various objects of the present invention, the invention is summarized as follows.

In accordance with the present invention, the elastic bandage of the present invention comprises an elastic, elongated material with an elongated length that is substantially longer than its width, in which the material has a portion that extends along its length that is a first color of a shade that is a function of the amount the material is stretched. In particular, the color is a first shade, which represents a loose fit when the bandage is wrapped around a body part in a loose configuration and the color is a second shade, which represents a firm fit when the bandage is wrapped around the body part in a firm configuration. The color may also be a third shade, which represents a tight fit. The particular fit of the bandage is identifiable based upon the shade of the color. As discussed below, another portion of the bandage, in another embodiment and variation, is a second color.

As an aspect of the present invention, a color chart is provided with the bandage and has printed thereon the first shade of the first color along with an adjacent notation that identifies a loose fit; and also has printed thereon the second shade of the first color along with an adjacent notation that identifies a firm fit. The color chart may further include the third shade of the color, which represents a tight fit.

As a feature of this aspect, instructions are provided for the user to use the color chart as a guide during wrapping of the elastic bandage on the body part.

As yet another aspect of the present invention, the bandage has a second portion that extends along the bandage's length, and the second portion is a second color that is substantially different from the first color. The width of the first portion is greater than the width of the second portion so that, when the elastic bandage is properly wrapped around the body part, most of the first color of the first portion is visible and nearly none of the second color of the second portion is visible. Preferably, none of the second color is visible except at the end of the wrapping.

In a preferred version, the first portion is roughly two-thirds the width of the elastic bandage, and the second portion is roughly one-third the width of the bandage.

As yet an additional aspect of the present invention, one side (i.e., a "first side") of the bandage is the first color and the other (second) side is a third color that is different from the first color. In addition, the elastic bandage includes an enclosure mechanism, such as a pair of metal clips or a hook and loop type fastener (i.e., Velcro), coupled to the end of the bandage for preventing the bandage from unraveling (or unwrapping), wherein the enclosure mechanism is able to secure the bandage (i.e., prevent it from unraveling) only if the bandage was wrapped with the second side having the third color disposed downward toward the body part. If the bandage is wrapped with the second side having the third color disposed upward away from the body part, then the enclosure mechanism is not able to be secured. Hence, this feature enables a user to easily place the proper side of the bandage down before wrapping it so that a standard clasping mechanism or Velcro enclosure can be properly used to secure the bandage upon completion of wrapping.

In accordance with another embodiment of the present invention, the aforementioned summarized elastic bandage, with its different aspects and features, doesn't include the feature that the shade of the bandage changes as the bandage is stretched. In other words, this embodiment pertains specifically to a bandage that includes the first and second portions of different colors that extend along the length of the bandage so that substantially all of the first color of the first portion is visible and substantially none of the second color of the second portion is visible when the elastic bandage is properly wrapped on a body part.

In accordance with a method embodiment of the present invention, a method of using an elastic bandage comprises the steps of providing an elastic bandage having the aforementioned feature that the shade of the bandage changes as it is stretched, and wrapping the elastic bandage around a body part in a manner so that the shade of the elastic bandage is maintained to be substantially consistent along the entire wrapped bandage.

Various aspects and features of this method embodiment include any of the above-summarized aspects and features, as applicable. This includes using a color chart while wrapping the bandage, providing a bandage with two colors along its length wherein most of the first color is visible and nearly none of the second color is visible upon completion of wrapping, and providing the second side of the bandage with a color that is different from the first color along with an enclosure wherein the bandage with the side having the third color is placed downward toward the body part prior to wrapping to enable the enclosure mechanism to properly secure the bandage upon completion of wrapping.

In accordance with a further method embodiment of the present invention, a method of using an elastic bandage comprises providing an elastic bandage with first and second portions having different colors extending along the bandage length, and wrapping the elastic bandage around a body party so that, upon completion of wrapping, substantially all of the first color of the first portion is visible and substantially none of the second color of the second portion is visible.

The above and various other objects, advantages and features of the present invention are discussed further below.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which.

DETAILED DESCRIPTION OF THE INVENTION

Figure 1:
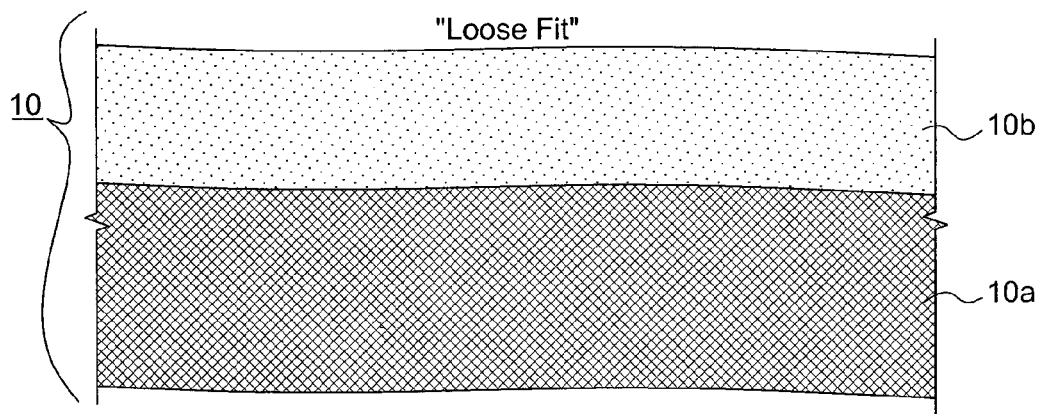
FIGS. 1, 2 and 3 schematically show portions of the elastic bandages of the present invention in different configurations.

As indicated above, the invention is directed to novel elastic bandages, as well as their manners of use, and particularly is directed to novel elastic bandages that provide beneficial features that are not provided by currently available elastic bandages.

The applicant of the present application has recognized the significance of improper application of elastic bandages and has invented the herein-described novel elastic bandage of the present invention, which provides certain advantages and benefits over existing devices, as discussed herein.

In accordance with the present invention, it is recognized that a properly used elastic bandage should: (a) apply a proper amount of pressure to an area of a person's body; (b) be properly placed around the body area; and (c) be properly applied so that the elastic bandage closure mechanism (e.g., the metal clip) may be appropriately used. In connection with feature (a), different injuries, recovering body parts, etc., require different amounts of pressure and, thus, a one-pressure fits all approach is not ideal and may result in further injury or at least an inhibition in the healing process. Moreover, different individuals perceive pressure differently and often are unable to judge the "ideal" pressure that should be applied by an elastic bandage. Some individuals tend to wrap an elastic bandage too tightly, which disadvantageously restricts blood circulation, causes additional pain, and potentially results in further injury and other undesirable effects. Other individuals tend to wrap elastic bandages too loosely, which often prevents proper bone mending and healing, and may cause irreversible permanent damage to tendons, ligaments and nerves. At best, a loosely wrapped bandage will reduce the effectiveness of the bandage.

In connection with the proper placement of the elastic bandage, a professionally wrapped elastic bandage advantageously applies a consistent amount of pressure along the entire body part that is wrapped, as well as minimizes discomfort and pain that would be caused by an improper wrapping. For example, an improperly wrapped elastic bandage may include wrinkles or gaps, which increase skin irritability, discomfort, inconsistent pressure to the injured body part, etc.

In the case of when an individual wraps an elastic bandage around a body part, and the elastic bandage includes a metal clip or Velcro as the fastening device, there is a reasonable likelihood that the individual will apply the bandage backwards, that is, with the wrong side down (facing the skin). The individual will discover the mistake upon fully wrapping the bandage (a process that could take upwards of a minute or two) as a result of the fastening mechanism not being usable, which results in the need to completely unwrap the bandage, turn it over, and the rewrap it again.

Turning now to the inventive Smart Bands elastic bandages, such bandages incorporate a number of novel features that enable individuals, who are not trained in wrapping elastic bandages, to wrap the elastic bandage in a manner that minimizes the problems encountered with existing devices.

Figure 2:
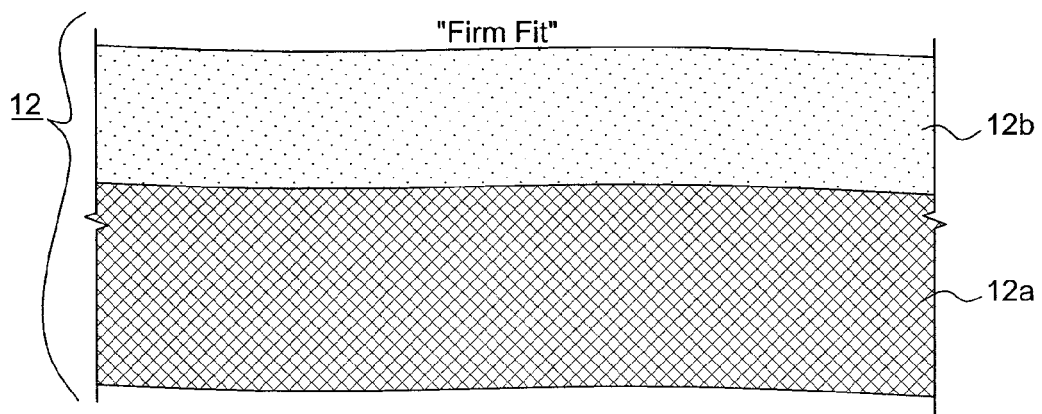
Figure 3:
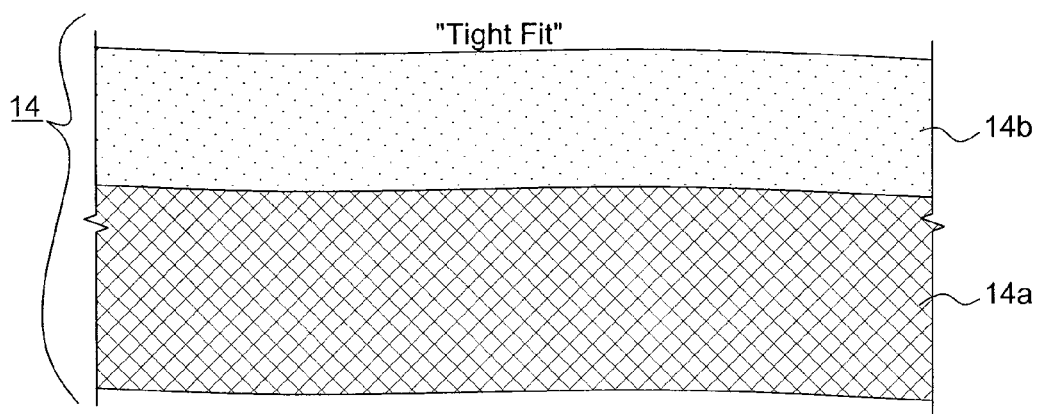

In accordance with feature (a) mentioned above—applying the proper amount of pressure—the Smart Bands elastic bandage has a portion along its entire length that changes color as it is stretched, thus enabling the amount of pressure that the bandage will apply to be identifiable. FIGS. 1, 2 and 3 of the accompanying drawings schematically show the Smart Bands elastic bandage in three different configurations.

FIG. 1 schematically shows a portion of bandage 10 in a "loose fit" configuration. As shown in FIG. 1, portion 10a of bandage 10 is green (the color green represented in the drawings by a diagonal cross-hatch pattern) and portion 10b is white (the color white represented by a dotted pattern). The significance of multiple colors is discussed below. In FIG. 1, portion 10a is particularly a dark green color (represented in the figure by a relatively small cross-hatch pattern), which indicates that the wrapped bandage is providing a relatively loose fit around the individual's body part.

FIG. 2 schematically shows a portion of bandage 12 in a "firm fit" configuration. Portion 12a of bandage 12 shown in FIG. 2 has a mid-range green color (represented in FIG. 2 by a larger cross-hatch pattern as compared to FIG. 1). The mid-range green color of portion 12a indicates that the bandage is providing a relatively firm fit, or relatively firm amount of pressure, to the wrapped part. Similar to FIG. 1, bandage 12 includes a white portion 12b.

FIG. 3 schematically shows a bandage 14 in a "tight fit" configuration, in which portion 14a has a light-green color (represented in FIG. 3 by a larger cross-hatch pattern as compared to FIG. 2). The light-green color of portion 14a indicates that the bandage is providing a relatively tight fit, or a relatively large amount of pressure as compared to the "firm fit" and "loose fit" configurations. Bandage 14 also includes white portion 14b.

Figure 4:
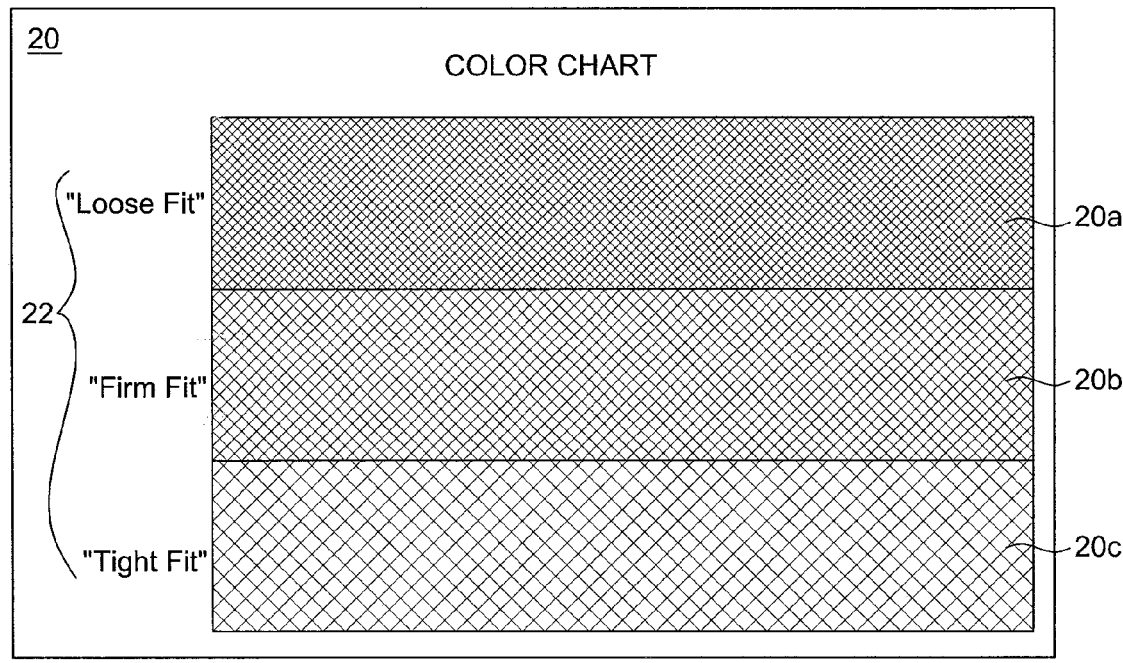
FIG. 4 is a schematic illustration of an exemplary color chart in accordance with the present invention.

In accordance with the present invention, it is recognized that non-trained individuals may need yet further guidance in assessing the amount of pressure that is being applied. The present invention thus provides, as a beneficial optional feature, a color chart to enable the individual to maintain a desired, consistent level of firmness/level of pressure as the bandage is being wrapped. An exemplary color chart 20 is schematically shown in FIG. 4. During use, and preferably based upon a medical provider's instructions as to whether the elastic bandage should be wrapped loosely, firmly or tightly, the individual wraps the herein-described novel elastic bandage and uses color chart 20 as a guide during wrapping. In particular, the individual wraps the bandage in a manner so that the color of the bandage is the same as one of the shades 22 on the color chart (e.g., shades 20a, 20b, 20c in FIG. 4). Like FIGS. 1-3, the different diagonal cross-hatch patterns shown in the color chart of FIG. 4 represent different shades. By adjusting the stretch of the bandage during wrapping, and by referring to the desired shade on the color chart, an individual is able to wrap the bandage so that it provides the proper amount of pressure to the wrapped body part. For example, if a loose fit is desired, the user wraps the bandage around the body part and stretches it while wrapping so that the bandage maintains a color shade that matches shade 20a shown on the color chart. If a firm fit is desired, the user stretches the bandage during wrapping so that the bandage maintains a color shade that matches shade 20b shown on the color chart. If a tight fit is desired, then the bandage is stretched during wrapping to match shade 20c.

In the event a medical provider uses the Smart Bands elastic bandage of the present invention when he/she professionally wraps the bandage on an individual, the individual or the medical provider can compare the color of the wrapped bandage to the color chart and make a notation next to the particular shade on the color chart that matches the actual shade of the color of the properly wrapped bandage. Then, at a later time, if it is necessary for the individual to remove the bandage, that individual may then properly re-wrap the bandage by referring to the color chart and wrapping the bandage so that its color is the same as the shade noted on the color chart.

Accordingly, in any of the above situations, the present invention enables individuals, who are not trained in applying elastic bandages, to be able to wrap the bandage in a manner that provides the desired degree of pressure to the area of interest. Moreover, with the use of both the color of the bandage as it is being wrapped and the color chart, the present invention enables individuals to be able to wrap the bandage so that it provides the precise amount of proper pressure in a manner that is consistent along the entire wrapping.

Figure 5:
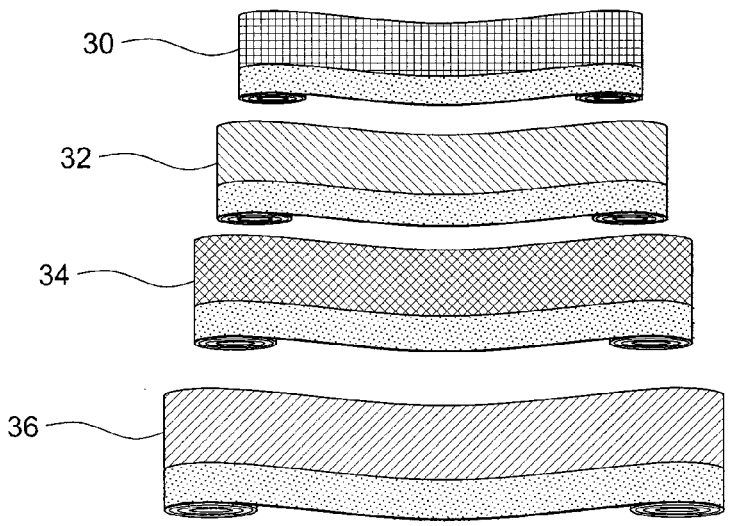
FIG. 5 shows other schematic illustrations representing other exemplary elastic bandages of the present invention.

As described herein, the Smart Bands elastic bandage includes a color along a portion of its entire length that changes color as it is stretched. This may be achieved by employing dyed elastic threads that reveal a meaningful change in color as they are stretched. Although FIGS. 1-3 and the color chart shown in FIG. 4 schematically illustrate different shades of green, other colors may be employed. For example, FIG. 5 schematically shows other exemplary novel elastic bandages 30, 32, 34, 36 of the present invention that are representative of yellow, orange, purple and blue bandages. Of course, other suitable colors may be employed.

In addition to the foregoing, the color chart may include more than three shades of a color. For example, the color chart may include four, five or more shades of the color of the bandage.

In accordance with a further feature and benefit of the present invention, the Smart Bands elastic bandage uses multiple colors, as particularly described below, to enable individuals to wrap or re-wrap a bandage that includes no gaps, wrinkles or lumps, thus minimizing skin irritability, discomfort and pain that would result from an improper wrapping, and further that provides sufficient consistent pressure along the entire body part that is wrapped.

As shown in FIGS. 1-3, as well as FIG. 5, the Smart Bands elastic bandage has a two-tone strip (e.g., 10a and 10b in FIG. 1) (also called "two-color system" herein) that extends along its entire length. It is noted that the figures show only a small length of the bandage. Typically, the Smart Bands elastic bandage will be rather long to allow the bandage to be wrapped multiple times around an arm, leg or other body part. Typical lengths include 54 inches, 72 inches or other appropriate length. As for the width of the Smart Bands elastic bandage, typical widths include 2.5 inches, 3 inches, 4 inches, 5 inches, 6 inches, or other width as appropriate.

As indicated above, one of the colors (e.g., the green strip 10a, 12a, 14a as shown in FIGS. 1-3) changes shade as it is stretched. The other color is white (the white strip 10b, 12b, 14b in FIGS. 1-3), which generally doesn't change shade as it is stretched, or generally changes shade in a manner that is less noticeable than the change of shade of the other color (as the bandage is stretched).

As shown in the figures, the portion of the elastic bandage that is green (for convenience, the "primary color" herein) extends roughly 60% along the bandage's width, and the portion that is white (the "secondary color") extends roughly 40% along the bandage's width. The relative widths of the color portions may be slightly different. For example, it is suitable for the primary color to extend ⅔ along the width and the secondary color to extend the remaining ⅓ of the bandage's width.

Figure 6:
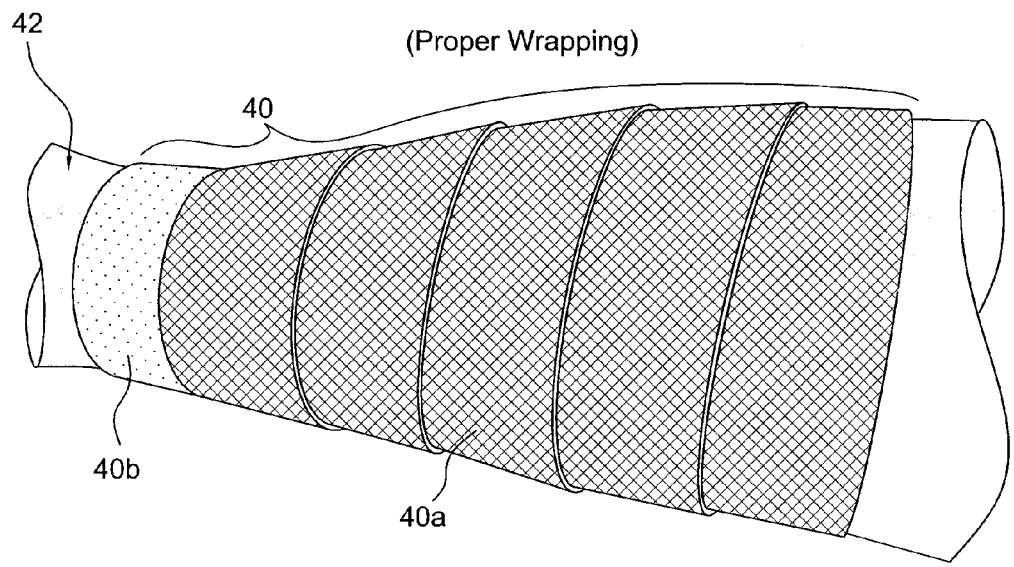
FIG. 6 schematically shows the elastic bandage of the present invention in a properly wrapped configuration.

During wrapping/application of the Smart Bands elastic bandage, the bandage is wrapped around the body part so that none of the secondary color (the schematically illustrated white portions shown in the figures) is visible (except at the very end of the wrapping), and the bulk of the primary color remains visible (i.e., is not hidden beneath the wrapping). A properly wrapped Smart Bands elastic bandage 40 is schematically shown in FIG. 6 (shown wrapped around an arm 42). As shown in FIG. 6, the visible part of bandage 40 is a single solid color (green portion 40*a*) until the very end of the bandage and then a small amount of white portion 40*b* is visible at the left end of the bandage wrapping. Optionally, that portion of the bandage that is white at the end (i.e., that is visible) after a proper wrapping can be made (e.g., dyed) green so that the entire, properly wrapped bandage is a single color. In such optional version, an individual using the color chart as discussed above can ensure that the entire bandage to the very end is applied at the correct pressure.

As illustrated in FIG. 6, by wrapping the bandage in the manner described above, the entire wrapping is wrinkle free, gap free and lump free, which in turn causes the wrapped elastic bandage to provide sufficient, consistent pressure to the wrapped body part, while at the same time providing a professionally wrapped appearance.

Figure 7:
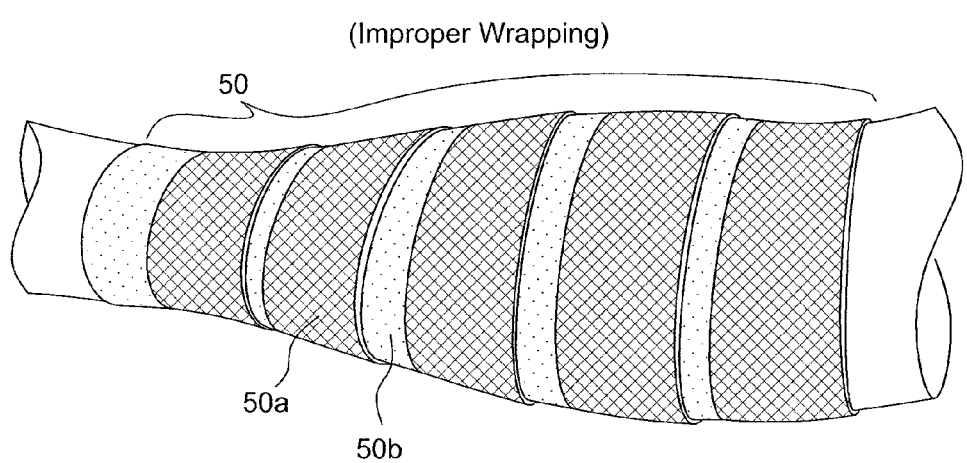
FIG. 7 schematically shows the elastic bandage of the present invention in an improperly wrapped configuration.

If, however, the Smart Bands elastic bandage is improperly wrapped, wherein some of the secondary color of the bandage remains visible during wrapping, the result of the wrapping is shown in FIG. 7. As schematically shown in FIG. 7, which has the appearance of a "barber pole" configuration, there is insufficient overlapping between the adjacent layers of the bandage 50, as evidenced by the visibility of the secondary (white) color 50*b* between each green portion 50*a*. This improper wrapping results in wrinkles but, worse, results in less pressure being applied to the body part than is intended or desired. Accordingly, the Smart Bands elastic bandage, by incorporating a two-color system, enables individuals, including individuals who are not trained in wrapping elastic bandages, to be able to properly and professionally wrap the elastic bandage around a body party.

As previously discussed, the primary color may be different than green. The secondary color also may be different than white, and may be beige or other similar somewhat-neutral color. The secondary color can also be a non-neutral color, but preferably should not distract the individual from concentrating on the shade of the primary color during the wrapping process.

In a variation, the Smart Bands elastic bandage can include a three-color system/version. In the three-color version, a relatively narrow third color stripe is disposed between the primary and second colors and is intended to be an additional guide during wrapping. In this variation, the individual wraps the bandage so that a portion of the third color is covered (e.g., about half of the third color) as the bandage is coiled/wrapped around the body part. The resulting appearance of a properly wrapped bandage of this three-color version is a solid green wrapping along the entire length except for the inclusion of a relatively thin third color (e.g., yellow) line that spirals around the wrapping. By employing three colors, with the third color being relatively narrow and disposed between the other two (primary and secondary) colors along the entire length of the bandage, wrapping the bandage in the manner described above nearly guarantees that the bandage will be completely and correctly applied.

In accordance with the present invention, wrapping the Smart Bands elastic bandage using the above-described two-color system (or three-color system), wherein the properly wrapped bandage appears as schematically shown in FIG. 6, such properly wrapped bandage further beneficially allows the proper use of heat or cold/ice packs to the wrapped area. In particular, during the application of heat or cold via a heat or ice pack (for convenience, "heat/ice pack") to a part of the body that is wrapped, the heat/ice pack most effectively treats the area when there is a low amount of temperature resistance (such temperature resistance being caused by excessive material) at the site. Accordingly, when the Smart Bands elastic bandage is wrapped so that most of the primary color (e.g., green) of the bandage is visible, as described herein, the resulting wrapped bandage does not contain an unnecessary amount of material on top of the site that requires the cold or heat treatment. Moreover, without providing an unnecessary extra amount of material over any part of the body that is wrapped, the skin that is wrapped is able to "breath."

Therefore, and in accordance with the present invention, when wrapping the Smart Bands elastic bandage, using both the color chart and the two-color system (or three-color system) as described above enables individuals to wrap the elastic bandage in a completely proper and professional manner, maximizes the effectiveness of the bandage resulting from the above-described proper and consistent pressure that is applied by the bandage, allows the more effective treatment of heat or cold to the wrapped area, and further enables the body part that is wrapped to be able breath.

As a further feature of the invention, the Smart Bands elastic bandage includes a closure mechanism, such as a metal clip or Velcro, to maintain the wrapped bandage upon being fully wrapped and a system for ensuring that the correct side of the bandage is contacting the body part (or other thing) being wrapped so that the closure mechanism may be properly used. In particular, the Smart Bands elastic bandage includes the above-discussed primary color only on a single side of the bandage and the other side of the bandage (also called "neutral side" herein) is white or other somewhat neutral color, and the user of the bandage is instructed to initially place the neutral side down (i.e., in contact with the skin or a device around which the elastic bandage is to be wrapped). By placing the neutral side down, thus keeping the side with the primary and secondary colors visible during wrapping, the elastic bandage is properly being used and then, upon completion of wrapping, the closure mechanism, which is designed to work only in this correct configuration, can properly hold the wrapped bandage in place.

Figure 8:
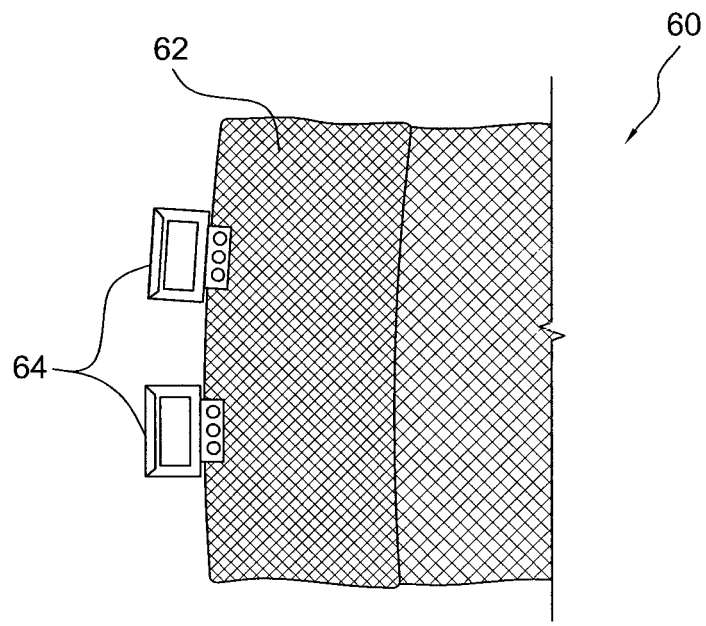
FIG. 8 schematically shows a pair of metal clips on an elastic bandage that may be used with the present invention.
Figure 9:
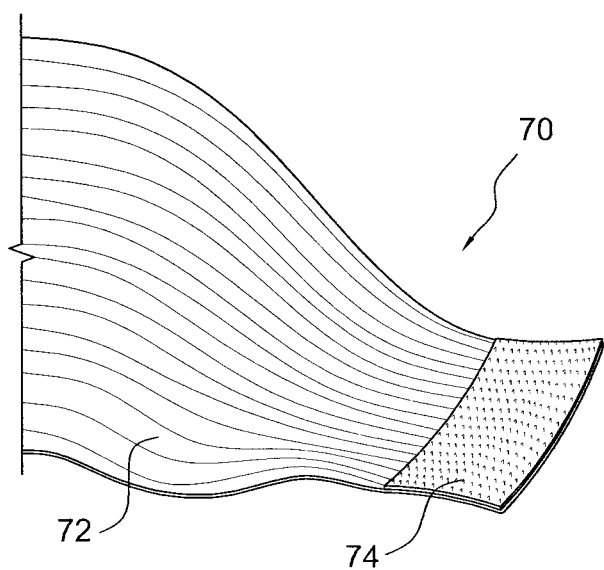
FIG. 9 schematically shows a Velcro connector on an elastic bandage that may be used with the present invention.

FIG. 8 shows a pair of standard metal clips 64 extending from a bandage portion 62 of elastic bandage 60 that may be used with the present invention. As shown, the bandage 60 must be used properly (with the proper side of the bandage face down) in order for the clips to work. Accordingly, by providing one side of the Smart Bands elastic bandage with a neutral color, which is placed against the body part or other item to be wrapped, the metal clips always will be in the correct configuration to properly maintain the wrapped bandage in place. Other closure mechanisms, including Velcro 74, such as that shown attached to the bandage portion 72 on bandage 70 in FIG. 9, that operate properly only when used in the correct configuration (i.e., with the correct side down) may also be used with the present invention. On the other hand, other types of closure mechanisms that work regardless of which side of the elastic bandage is face down also may be used with the present invention and, in such case, it is not necessary for the appearance of the two sides of the bandage to be different.

In yet another variation, the Smart Bands elastic bandage is "self adhesive" and, thus, does not include a separate closure mechanism. By being self adhesive, the bandage will adhere to itself as it wrapped around the body part. Accordingly, in this self-adhesive version, it is not necessary for the appearance of the two sides of the bandage to be different.

From the foregoing, it is illustrated that the Smart Bands elastic bandages of the present invention offer a number of features and benefits that are not provided by currently available elastic bandages. The Smart Bands elastic bandages have features that: enable any individual, particularly individuals who are not trained to apply elastic bandages, to wrap the bandage in a manner so that the proper amount of pressure is applied to the body part being wrapped; to remove the guesswork that ordinarily is required in applying these types of bandages; to enable any individual to properly wrap the bandage so that there are no lumps, wrinkles or gaps; to enable the proper application of heat or cold to the wrapped part of the body wherein the bandage is wrapped in a manner that allows the heat or cold to be able to properly pass through the bandage; to enable any individual to quickly ascertain which side of the bandage is placed down in order for the attached closure mechanism to properly work; and to, all in all, apply the bandage in a manner that maximizes the desired affectivity and to minimize any negative impact that ordinarily would result from an improperly wrapped bandage.

In view of the description provided herein, the present invention may be summarized by an elastic bandage having an elongated length that is substantially longer than its width and having a front (or first) side representing an up side that does not come into contact with an item, such as a body part, to be wrapped, and a bottom (or second) side representing a down side that is placed in contact with the item to be wrapped, in which at least one of the first or second sides of the bandage includes at least two colors, a primary color and a secondary color, the primary and second colors extending at least substantially along the entire length of the bandage, the primary color extending across at least 50% of the bandage width, and the secondary color extending across the remaining part of the bandage width, and the primary color changing shade, which is visible to a user of the bandage, as the bandage is stretched.

Preferably, the primary color extends across roughly or substantially two-thirds of the bandage width, in the range of between 60% and 70% of the bandage width.

Optionally, the bandage includes a permanently attached closure mechanism that is able to maintain the bandage when fully wrapped with the bandage bottom side is placed down and in contact with the item being wrapped, and the down side of the bandage does not include the primary color, wherein the primary color is provided only on the bandage up side, to act as a guide to a user to place the side without the primary color down during use.

The elastic bandage of the invention is provided with a color chart to aid the user in wrapping the bandage with the proper amount of stretch, thus providing the proper amount of pressure to the item being wrapped, by comparing the shade of the primary color to the color chart during wrapping. The color chart contains at least three shades of the primary color respectively representing a loose fit, firm fit, and tight fit.

In a method of applying the elastic bandage of the invention, a user wraps the bandage with the side with the primary color up and wraps or coils the bandage in a manner in which: (a) the shade of the primary color matches a selected shade identified on the color chart; and (b) no amount of the secondary color is visible in the wrapped bandage, except for a small portion of the bandage at its end.

Preferably, during wrapping, most of the primary color of the bandage remains visible.

In the event the bandage includes a permanently attached closure mechanism that is able to maintain the bandage when fully wrapped, before wrapping the bandage, the side of the bandage that does not contain the primary color is placed face down in contact with the item being wrapped, thus allowing the closure mechanism to be properly used upon completion of the wrapping.

Other features that may be incorporated are as described above.

The present invention has been described in the context of a number of embodiments, and multiple variations and examples thereof. It is to be understood, however, that other expedients known to those skilled in the art or disclosed herein may be employed without departing from the spirit of the invention.

Therefore, it is intended that the appended claims be interpreted as including the embodiments described herein, the alternatives mentioned above, and all equivalents thereto.

What is claimed is:

1. An elastic bandage, comprising:
   an elastic, elongated material having an elongated length substantially longer than a width of the material;
   the material having a portion thereof extending along the length that is a first color that is of a shade that is a function of an amount the material is stretched, the first color being a first shade representing a loose fit when the material is wrapped around a part of a body in a loose configuration, the first color being a second shade representing a firm fit when the material is wrapped around the part of the body in a firm configuration, so that a fit of the material is identifiable by a user of the elastic bandage based upon the shade of the first color,
   the portion extending along the length of the material representing a first portion, the portion extending continuously along an entire length of the material, the material having a second portion extending along the length that is a second color substantially different from the first color, a width of the first portion being greater than a width of the second portion so that substantially all of the first color of the first portion is visible and substantially none of the second color of the second portion is visible when the elastic bandage is properly wrapped on a body part.

2. The elastic bandage of claim 1, wherein the first color is a third shade representing a tight fit when the material is wrapped around the part of the body in a tight configuration.

3. A system comprising:
   the elastic bandage of claim 1, and
   a color chart having printed thereon:
   substantially the first shade of the first color along with a first notation adjacent the first shade representing a loose fit; and
   substantially the second shade of the first color along with a second notation adjacent the second shade representing a firm fit.

4. The system of claim 3, further comprising instructions for the user to use the color chart as a guide during wrapping of the elastic bandage on a body part.

5. The elastic bandage of claim 1, wherein the width of the first portion is substantially two-thirds of the width of the material and the width of the second portion is substantially one-third of the width of the material.

6. The elastic bandage of claim 1, wherein the material has first and second sides, the first side having the first color and the second side having a third color substantially different from the first color, the elastic bandage further comprising an enclosure mechanism coupled to an end of the material for preventing the elastic bandage from unwrapping if the elastic bandage is wrapped with the second side having the third color disposed downward toward the body part, the enclosure mechanism not being capable of preventing the elastic bandage from unwrapping if the elastic bandage is wrapped with the second side having the third color disposed upward not toward the body part.

7. The elastic bandage of claim 6, wherein the enclosure mechanism is a pair of metal clips.

8. The elastic bandage of claim 6, wherein the enclosure mechanism is a hook and loop fastener.

9. An elastic bandage, comprising:
an elastic, elongated material having an elongated length substantially longer than a width of the material;
the material having first and second portions extending along the length of the material, the first portion being a first color and the second portion being a second color substantially different from the first color, the first portion extending continuously along an entire length of the material;
a width of the first portion being greater than a width of the second portion so that substantially all of the first color of the first portion is visible and substantially none of the second color of the second portion is visible when the elastic bandage is properly wrapped on a body part.

10. A method of using an elastic bandage, comprising:
providing an elastic bandage, a length of the elastic bandage being substantially longer than a width of the elastic bandage, the elastic bandage having a portion thereof extending along the length that is a first color that is of a shade that is a function of an amount the elastic bandage is stretched; and
wrapping the elastic bandage around a part of a body in a manner wherein the shade of the first color of the elastic bandage is maintained to be substantially consistent along the entire wrapped bandage, the shade of the first color being one of at least first and second shades, the first shade representing a loose fit and the second shade representing a firm fit,
the portion extending along the length of the elastic bandage representing a first portion, the first portion extending continuously along an entire length of the material, the elastic bandage having a second portion extending along the length that is a second color substantially different from the first color, a width of the first portion being greater than a width of the second portion;
the wrapping step comprising wrapping the elastic bandage around the part of the body in a manner wherein, upon completion of wrapping, substantially all of the first color of the first portion is visible and substantially none of the second color of the second portion is visible.

11. The method of claim 10, wherein the shade of the first color being one of the first shade, the second shade and a third shade, the third shade representing a tight fit.

12. The method of claim 10, further comprising providing a color chart having printed thereon:
substantially the first shade of the first color representing a loose fit; and
substantially the second shade of the first color representing a firm fit;
wherein the wrapping step comprises wrapping the elastic bandage around the part of the body while referring to one of the shades printed on the color chart and maintaining the shade of the elastic bandage during wrapping to be substantially the same as to the referred shade printed on the color chart.

13. The method of claim 12, wherein the color chart has further printed thereon a first notation adjacent the first shade identifying a loose fit, and a second notation adjacent the second shade identifying a firm fit.

14. The method of claim 12, wherein the color chart has further printed thereon substantially a third shade of the first color representing a tight fit.

15. The method of claim 10, wherein the width of the first portion is substantially two-thirds of the width of the elastic bandage and the width of the second portion is substantially one-third of the width of the elastic bandage.

16. The method of claim 10, wherein the material has first and second sides, the first side having the first color and the second side having a third color substantially different from the first color, the elastic bandage further comprising an enclosure mechanism;
the method further comprising the steps of:
placing, prior to wrapping, the second side of the elastic bandage having the third color downward toward the part of the body to be wrapped; and
securing, upon completion of wrapping, the enclosure mechanism to prevent the elastic bandage from unwrapping, wherein the enclosure mechanism is unable to be secured to prevent the elastic bandage from unwrapping if the second side of the elastic bandage having the third color is placed, prior to wrapping, upward away from the part of the body to be wrapped.

17. A method of using an elastic bandage, comprising:
providing an elastic bandage, a length of the elastic bandage being substantially longer than a width of the elastic bandage, the elastic bandage having first and second portions extending along the length of the material, the first portion being a first color and the second portion being a second color substantially different from the first color, the first portion extending continuously along an entire length of the material; and
wrapping the elastic bandage around a part of a body in a manner wherein, upon completion of wrapping, substantially all of the first color of the first portion is visible and substantially none of the second color of the second portion is visible.

* * * * *